US010286163B1

(12) United States Patent
Paustian et al.

(10) Patent No.: US 10,286,163 B1
(45) Date of Patent: May 14, 2019

(54) ON DEMAND AEROSOLIZED DELIVERY INHALER

(71) Applicants: Philip J. Paustian, Panama City, FL (US); Robert J. Hughes, Lynn Haven, FL (US)

(72) Inventors: Philip J. Paustian, Panama City, FL (US); Robert J. Hughes, Lynn Haven, FL (US)

( * ) Notice: Subject to any disclaimer, the term of this patent is extended or adjusted under 35 U.S.C. 154(b) by 558 days.

(21) Appl. No.: 14/521,504

(22) Filed: Oct. 23, 2014

Related U.S. Application Data

(60) Provisional application No. 61/947,636, filed on Mar. 4, 2014.

(51) Int. Cl.
*A61M 11/02* (2006.01)
*A61M 15/00* (2006.01)

(52) U.S. Cl.
CPC ........ *A61M 15/0091* (2013.01); *A61M 11/02* (2013.01); *A61M 15/0003* (2014.02); *A61M 15/009* (2013.01); *A61M 15/0021* (2014.02); *A61M 2202/0007* (2013.01); *A61M 2202/04* (2013.01); *A61M 2205/07* (2013.01); *A61M 2205/12* (2013.01); *A61M 2205/3303* (2013.01); *A61M 2205/3344* (2013.01); *A61M 2205/50* (2013.01); *A61M 2205/8206* (2013.01)

(58) Field of Classification Search
CPC .... A61M 11/00; A61M 11/005; A61M 11/02; A61M 11/06; A61M 11/08; A61M 15/0003; A61M 15/0021; A61M 15/0085; A61M 15/009; A61M 15/0091
See application file for complete search history.

(56) References Cited

U.S. PATENT DOCUMENTS

| 2,906,513 | A | * | 9/1959 | Tabor | ..................... A61M 11/06 239/515 |
| 3,223,289 | A | * | 12/1965 | Bouet | ..................... A45D 40/00 141/24 |
| 3,311,125 | A | * | 3/1967 | Beasley | ................ A61M 16/16 116/268 |
| 3,356,088 | A | * | 12/1967 | Nelson | ................ A61M 16/147 128/200.23 |

(Continued)

FOREIGN PATENT DOCUMENTS

DE    102008050218 A1 *  7/2009   ............ A61M 11/06
JP   WO 2007105492 A1 *  9/2007   ........... A61H 33/063

(Continued)

OTHER PUBLICATIONS

Puritan Bennet 7200 series operators manual, Sep. 1990.*

*Primary Examiner* — Kathryn E Ditmer
(74) *Attorney, Agent, or Firm* — James Creighton Wray; Meera P. Narasimhan

(57) ABSTRACT

A hand-held aerosolized inhaler that delivers an aerosolized solution to the user on demand when he or she inhales is provided. A pressure or flow sensor within the invention detects the change in air flow as the user inhales and triggers spraying the aerosol solution only when the inhaled breath stream will optimally entrain the sprayed aerosol. The pressure or flow sensor sends an electronic signal to turn on or off liquid and air pumps as the user breathes. Liquid, or liquid and air are pumped to the nozzle inside the invention to create an aerosolized mixture.

24 Claims, 4 Drawing Sheets

(56) References Cited

U.S. PATENT DOCUMENTS

| | | | | |
|---|---|---|---|---|
| 3,539,102 | A | * | 11/1970 | Lang .................. A61M 11/00 239/4 |
| 4,629,478 | A | * | 12/1986 | Browner ............. B01F 3/04007 239/434 |
| 5,156,776 | A | * | 10/1992 | Loedding ............... A61M 11/00 128/203.12 |
| 5,363,842 | A | | 11/1994 | Mishelevich et al. |
| 5,520,166 | A | | 5/1996 | Ritson et al. |
| 5,666,947 | A | * | 9/1997 | McKay .............. A61M 15/0065 128/200.14 |
| 5,743,252 | A | | 4/1998 | Rubsamen et al. |
| 5,941,241 | A | | 8/1999 | Weinstein et al. |
| 6,076,519 | A | | 6/2000 | Johnson |
| 6,367,470 | B1 | | 4/2002 | Denyer et al. |
| 6,571,790 | B1 | | 6/2003 | Weinstein |
| 6,584,971 | B1 | | 7/2003 | Denyer et al. |
| 6,606,989 | B1 | * | 8/2003 | Brand ................. A61M 11/005 128/200.16 |
| 6,684,880 | B2 | * | 2/2004 | Trueba .............. A61M 15/0085 128/200.16 |
| 6,739,332 | B1 | * | 5/2004 | Higenbottann ....... A61M 11/06 128/200.13 |
| 6,792,939 | B1 | | 9/2004 | Weinstein |
| 6,851,626 | B2 | | 2/2005 | Patel et al. |
| 6,854,461 | B2 | | 2/2005 | Nichols et al. |
| 6,904,907 | B2 | | 6/2005 | Speldrich et al. |
| 7,342,660 | B2 | * | 3/2008 | Altobelli .................. A61B 5/08 356/338 |
| 7,458,373 | B2 | | 12/2008 | Nichols et al. |
| 7,708,011 | B2 | * | 5/2010 | Hochrainer ....... A61M 15/0028 128/200.14 |
| 7,712,466 | B2 | | 5/2010 | Addington et al. |
| 7,726,306 | B2 | | 6/2010 | Addington et al. |
| 7,802,569 | B2 | | 9/2010 | Yeates et al. |
| 8,015,969 | B2 | | 9/2011 | Abrams |
| 8,109,266 | B2 | | 2/2012 | Addington et al. |
| 8,333,190 | B2 | | 12/2012 | Addington et al. |
| 8,474,452 | B2 | | 7/2013 | Gumaste et al. |
| 2002/0020412 | A1 | * | 2/2002 | Gilbert .................. A61M 11/06 128/203.12 |
| 2003/0101991 | A1 | * | 6/2003 | Trueba .............. A61M 15/0085 128/200.14 |
| 2003/0196660 | A1 | * | 10/2003 | Haveri .............. A61M 15/0085 128/203.12 |
| 2004/0134494 | A1 | * | 7/2004 | Papania ............... A61M 11/005 128/203.12 |
| 2005/0155602 | A1 | * | 7/2005 | Lipp ................. A61M 15/0065 128/203.12 |
| 2005/0244339 | A1 | * | 11/2005 | Jauernig ............... A61K 9/0078 424/45 |
| 2005/0265060 | A1 | * | 12/2005 | Nobunaga ........... G11C 7/1072 365/15 |
| 2006/0243274 | A1 | * | 11/2006 | Lieberman ........... A61M 11/005 128/200.14 |
| 2008/0092880 | A1 | * | 4/2008 | Ooida .................. A61M 11/005 128/200.14 |
| 2009/0126722 | A1 | * | 5/2009 | Sugita ................. A61K 9/0073 128/200.19 |
| 2009/0139520 | A1 | * | 6/2009 | Weaver ................ A61M 11/041 128/203.12 |
| 2009/0178672 | A1 | | 7/2009 | Mullinger et al. |
| 2009/0212133 | A1 | * | 8/2009 | Collins, Jr. .......... A61M 11/005 239/338 |
| 2012/0167878 | A1 | * | 7/2012 | Belson ..................... A61F 7/12 128/200.16 |
| 2012/0186582 | A1 | | 7/2012 | Addington et al. |
| 2013/0192594 | A1 | | 8/2013 | Addington et al. |
| 2014/0166781 | A1 | * | 6/2014 | Johnson ................. A61L 9/127 239/310 |

FOREIGN PATENT DOCUMENTS

| | | |
|---|---|---|
| WO | 2011003017 A1 | 1/2011 |
| WO | 2012100164 A1 | 7/2012 |
| WO | 2013076654 A1 | 5/2013 |

\* cited by examiner

ON DEMAND AEROSOLIZED DELIVERY INHALER

This application claims the benefit of U.S. Provisional Application No. 61/947,636 filed Mar. 4, 2014, which is hereby incorporated by reference in its entirety.

BACKGROUND OF THE INVENTION

Aerosolized inhalers are used on a daily basis for a wide range of medical treatments. Conventional inhalers use volatile organic compounds, pressurized gases, or large amounts of heat to produce vaporization and deliver of aerosols. Needs exist for an aerosolized delivery inhaler that optimizes the delivery of aerosol without requiring volatile compounds, pressurized gases, or large amounts of heat.

SUMMARY OF THE INVENTION

The invention provides a hand-held aerosolizer that delivers an aerosolized solution to the user when he or she inhales. The invention uses an air pump that eliminates the need for volatile organic compounds, pressurized gases, or large amounts of heat to produce vaporization that are integral to conventional hand-held aerosol generating systems and electronic cigarettes. A pressure or flow sensor detects the change in pressure or flow through the invention as the user inhales and this triggers pump activation. This mechanism causes the aerosol solution to spray only while the inhaled breath stream optimally entrains the sprayed aerosol.

Replacing oral or parenteral medication delivery with inhalation may allow for more rapid and convenient administration of medicaments. The nauseated post-chemotherapy patient or severely seasick individual during cruises, fishing, or diving trips cannot retain oral medication due to ongoing emesis. However, under such adverse conditions the user will still be able to inhale, which, with this invention will allow him to gain control over his symptoms. Unlike conventional metered dose inhalers, the present invention does not require the use of special breathing techniques. A conventional nebulizer requires a large power source to drive it. The present invention removes the burden of a large power source while still effectively nebulizing the desired fluid. The present invention is also an improvement on the conventional nebulizer in that it the medication is delivered through a mouthpiece instead of a mask.

Small droplets are created in the aerosolization process and travel in the inhalation stream. The droplets may measure 1 mm or less. This size allows them to traverse the entire bronchial tree to reach even the most peripheral lung alveoli. The invention can be configured to deliver simultaneously different aerosol solutions to the nose and mouth to optimize the delivery of medication by creating a more pleasant experience. Using control circuitry, the invention is able to deliver a measured dose per inhalation or deliver a proper dose over multiple breaths. In some cases, multiple compounds need to be delivered yet may not be compatible in one solution. The present invention allows these compounds or medications to be inhaled without being made into one solution. The present invention can be configured with multiple liquid pumps and corresponding cartridges to allow for this method of delivery. The control circuitry of the invention can create the required ratio of substances by mixing the fluids as they are aerosolized in the mixing nozzle. For a range of dispensing applications by changing the nozzle system the size of the air pump can be reduced or the air pump can be eliminated with a corresponding increase in liquid pump operating pressure thus allowing larger fluid reservoirs in the same form factor device.

The sensor within the mouthpiece of the current invention detects when the user is inhaling and may activate twin battery operated fluid and air pumps that connect to the mixing nozzle. The pumps release the aerosol as long as the user continues to inhale at a sufficient inhalation rate for entrainment. When the user inhales, the sensor circuitry creates a controllable lag time for the activation or deactivation of the pumps. The invention will typically be set so that the user does not perceive any lag time. The device through appropriately programming micro controller circuitry can reduce risk for user overdosage. Additional safety derives from automatically stopping the stream of aerosol release when the user is not inhaling at a sufficient rate. This also avoids wasting product, counting it as delivered when it is not, and the potential accumulation of fluid in the nozzle or in other components of the invention.

In an alternative embodiment, a compressed air cartridge replaces the batteries used to supply sufficient air volume at pressure. Regulated air pressure from the compressed air cartridge replaces the air pump as the pressurized air source. Compressed air energy also drives the fluid pump. By utilizing compressed air, the current invention avoids the issues associated with battery use. Compressed air may be used to generate sufficient electric power to operate the micro-controller circuitry.

In its simplest embodiment, a small aerosol inhaler has two battery-operated pumps: an air pump and a liquid pump. The liquid to be aerosolized is stored in a collapsible fluid reservoir within a removable cartridge. A small tube extends from this cartridge receiver to permit flow from the reservoir to an input of the liquid pump. Pressurized fluid flows from the pump via another tube to the mixing nozzle. The air pump pulls filtered air from the atmosphere, compresses it, and delivers the compressed gas via a tube to the mixing nozzle. The aerosol exits from the mixing nozzle to the air passage way. In this portion of the air pathway inhaled air entrains the released aerosol and together the mixture travels to the mouthpiece.

In this embodiment a pressure sensor within the inhalation air passageway detects when the user is inhaling. This sensor triggers control circuitry to turn the pumps on and off to deliver the aerosol for as long as the user is inhaling at a sufficient rate for entrainment. This mechanism prevents solution loss after the user stops inhaling and avoids the accumulation of solution in the inhalation passageway.

When the device's air flow sensing system detects the minimum adequate inhalation to maintain entrainment the pumping system is triggered. The diversion of a small amount of air to flow over a scent source can offer the user additional sensory stimulation. Adding finely divided solids in a semi-permeable membranous bag in the liquid reservoir can be done to continuously to reinforce active product in the orally inhaled solution, potentially enhancing shelf life. For delivery of medications, controller circuitry allows regulation of dose distribution over time or per breath and product recognition from RFID tagging or similar technology to identify cartridges. The present invention can be programmed to release medicaments under prescribed intervals or parameters permitting use in patient-controlled analgesia, anti-nausea, motion sickness, phophodiesterase-5 inhibitors for erectile dysfunction or other therapeutic applications. It is also optimal for delivering inhaled alcoholic spirits such as vodka, tobacco extracts, and other mood altering substances as they become legal. For the user, it will just be a matter of selecting the cartridge for current need, therapy or pleasure.

These and further and other objects and features of the invention are apparent in the disclosure, which includes the above and ongoing written specification, with the drawings.

DETAILED DESCRIPTION

Figure 2:
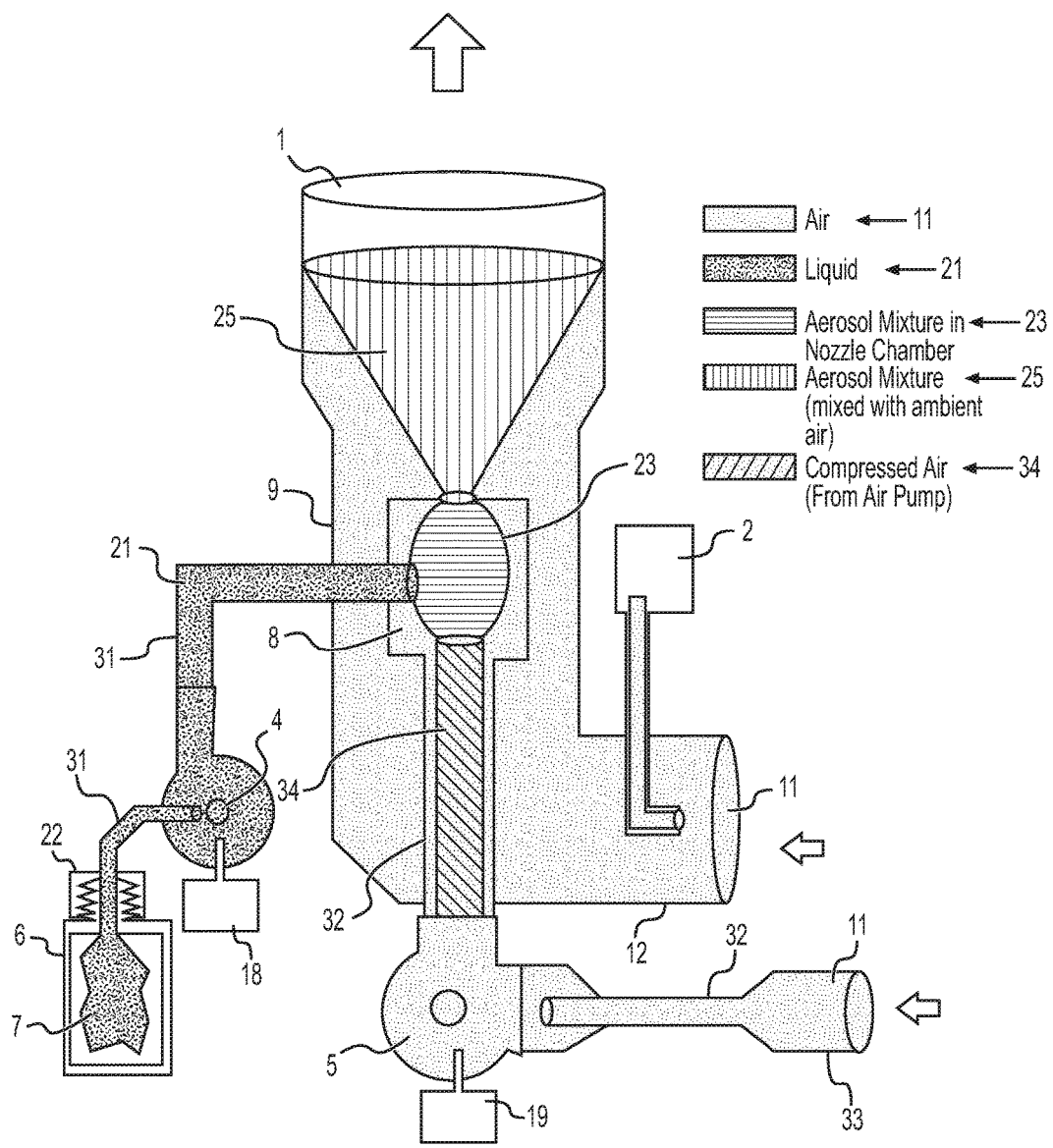
FIG. 2 is a schematic representation of the hand held device.

The following item numbers relate to the drawings.
1 Mouthpiece
2 Sensor
3 op-amp/comparator circuit
4 Liquid Pump
5 Air Pump
6 Cartridge
7 Collapsible Reservoir
8 Mixing Nozzle
9 Throat for aerosol entrainment
10 Sine Wave Symbol representing negative pressure of inhalation
11 Ambient Air or Atmospheric Air (Dot Texture)
12 Air Passage to direct outside air 11 past sensor 2
13 motor control unit for air pump
14 motor control unit for liquid pump
15 batteries
16 microcontroller
18 pump motor for liquid pump 4
19 pump motor for air pump 5
20 Inhalation Pressure Signature (Suction Breathing Signature)
21 liquid (wave texture)
22 cartridge receiver
23 liquid and air mixing in mixing nozzle chamber (darker bubble texture)
25 aerosol mixture mixed with ambient air drawn into the mouthpiece (lighter bubble texture)
26 sensor activated on/off transistor switch
27 transformer battery charger assembly
28 voltage differential from sensor
29 inhalation flow velocity
30 charging circuitry
31 product conduit
32 air conduit
33 air pump inlet
34 compressed air FIG. 1 is a functional schematic of the invention, showing relationships between electrical and mechanical parts. A mouthpiece 1 for inhaling ambient air 11 and an atomized mixture 23 of air and a liquid mist are shown in mixing nozzle 8. A sensor 2, sensing the pressure or flow of incoming ambient air 11, provides an electronic signal to control coordinated liquid pump 4 and air pump 5 action by supplying battery power to motors 18 and 19. Liquid 21 stored in a collapsible reservoir 7 within removable cartridge 6 is drawn via negative pressure generated by the liquid pump 4. The liquid pump 4 delivers pressurized fluid to the mixing nozzle 8 via product conduit 31 by drawing the fluid out of the collapsible reservoir 7 which resides in cartridge 6. The air pump 5 pulls filtered air from the atmosphere through air pump inlet 33, compresses it, and delivers the compressed air 34 via air conduit 32 to the mixing nozzle 8. An air and product mixture is formed in mixing nozzle 8. The mix 23 exits from the mixing nozzle 8 into the mouthpiece 1. Ambient air 11 flows inward to mouthpiece 1 through a throat 9 for aerosol entrainment 25 of the mix 23.

Drawing air with a user's mouth through mouthpiece 1 activates sensor 2, and sensor 2 actuates motors 18 and 19 to drive liquid and air pumps 4 and 5 to pump liquid from collapsible reservoir 7 in cartridge 6 and air 11 into mixing nozzle 8.

Negative pressure of inhalation, represented by the negative portion of sine wave symbol 10, triggers a change in pressure detected by the pressure sensor module 2, which sends an electrical impulse as a voltage differential 28 to the op-amp/comparator circuit 3. The comparator portion of the op-amp/comparator circuit electronically turns on or off the liquid pump 4 and the air pump 5 to maintain aerosol dispensing only when inhalation negative pressure is sufficient to insure adequate entrainment to deliver the inhaled product aerosol mixture from the liquid reservoir 7 in cartridge 6 to the lung. An on/off diaphragm pressure switch may be used for aerosolization spray activation. Breathing pressure signature creates air flow through the device. The plot in the lower left of FIG. 1 shows development of positive and negative pressure relative to diaphragm neutral position. Flow through the device is created by negative pressure sections of sine wave (below 0 on the plot). The pressure signature creates corresponding flow through the device.

The mixing nozzle 8 mixes compressed atmospheric air 34 from the air pump 5 and liquid 21 from the liquid pump 4 and releases the mix 25 that is entrained in the inhalation stream through the mouth piece 1. The mouthpiece 1 draws atmospheric air 11 from outside air through an air passage 12 that directs the inhaled atmospheric air 11 past sensor 2 and around the mixing nozzle 8. This channels air to optimize entrainment of the aerosolized fluid mixed with air in the mixing nozzle 8 creating the entrained mix of ambient air 11 and aerosolized fluid mixed with air 25.

Pump motor 19 powers air pump 5 while pump motor 18 powers liquid pump 4. Pump motors 18 and 19 are supplied with separate motor control units: motor control unit 13 for air pump motor 19 and motor control unit 14 for liquid pump motor 18. These motor control units contain the necessary voltage regulation and pulse width modulation circuitry to insure accurate liquid delivery and optimum power use. To meter flow for pharmacologic applications, the motor control units may incorporate one or more stepper motors or servo motor controllers to precisely meter and record the liquid quantity delivered, the inhalation pressure required, and the time events occurred. These additional functions entail the addition of a low power, low cost microcontroller 16. Side lines on microcontroller 10 are micro controller input/output lines to sensing, motor control and other advanced features as needed.

Power for the invention comes from batteries 15 which can be replaceable, rechargeable, or rechargeable in the system.

FIG. 2 illustrates the flow of air 11 and liquid 21, from the atmosphere and the collapsible reservoir 7 in cartridge 6 respectively, into the mixing nozzle 8. An air pump 5 compresses the atmospheric air 11 prior to its mixing with the target liquid 21 in the mixing nozzle 8 to produce a mixture of the product and compressed air 23 to be released from the mixing nozzle 8 as a mix. In FIG. 2, air flow is represented by a dotted texture, compressed air is represented by a dotted texture with diagonal lines 34 coming from air pump 5 inside the air conduit 32 and in mixing nozzle 8, liquid is represented by a wave texture 21, the mixture is represented by a darker bubble texture 23, and the aerosol mixture mixed with ambient air drawn into the mouthpiece is represented by a lighter bubble texture 25.

Figure 3:
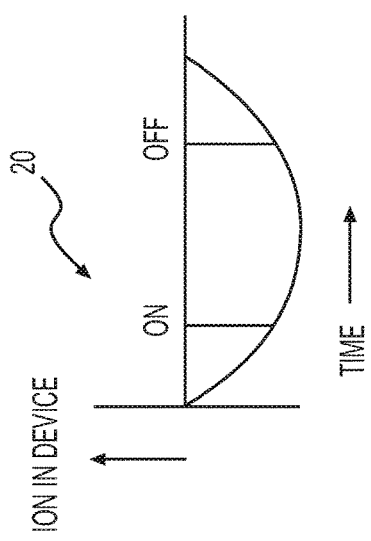
FIG. 3 shows on-off limits of a suction breathing signature.

In FIG. 3, the sensor module 2 allows the motor controllers 13 and 14 to respond to the inhalation pressure signature 20 to turn on and off to maintain aerosol 23 dispensing only when inhalation air flow 11 is adequate to maintain entrainment.

Figure 4:
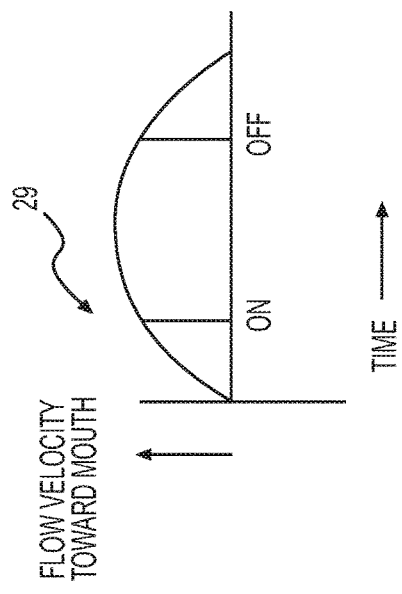
FIG. 4 shows inhalation flow velocity towards the mouth.

FIG. 4 shows inhalation flow velocity 29 towards mouth due to negative pressure over time.

Figure 1:
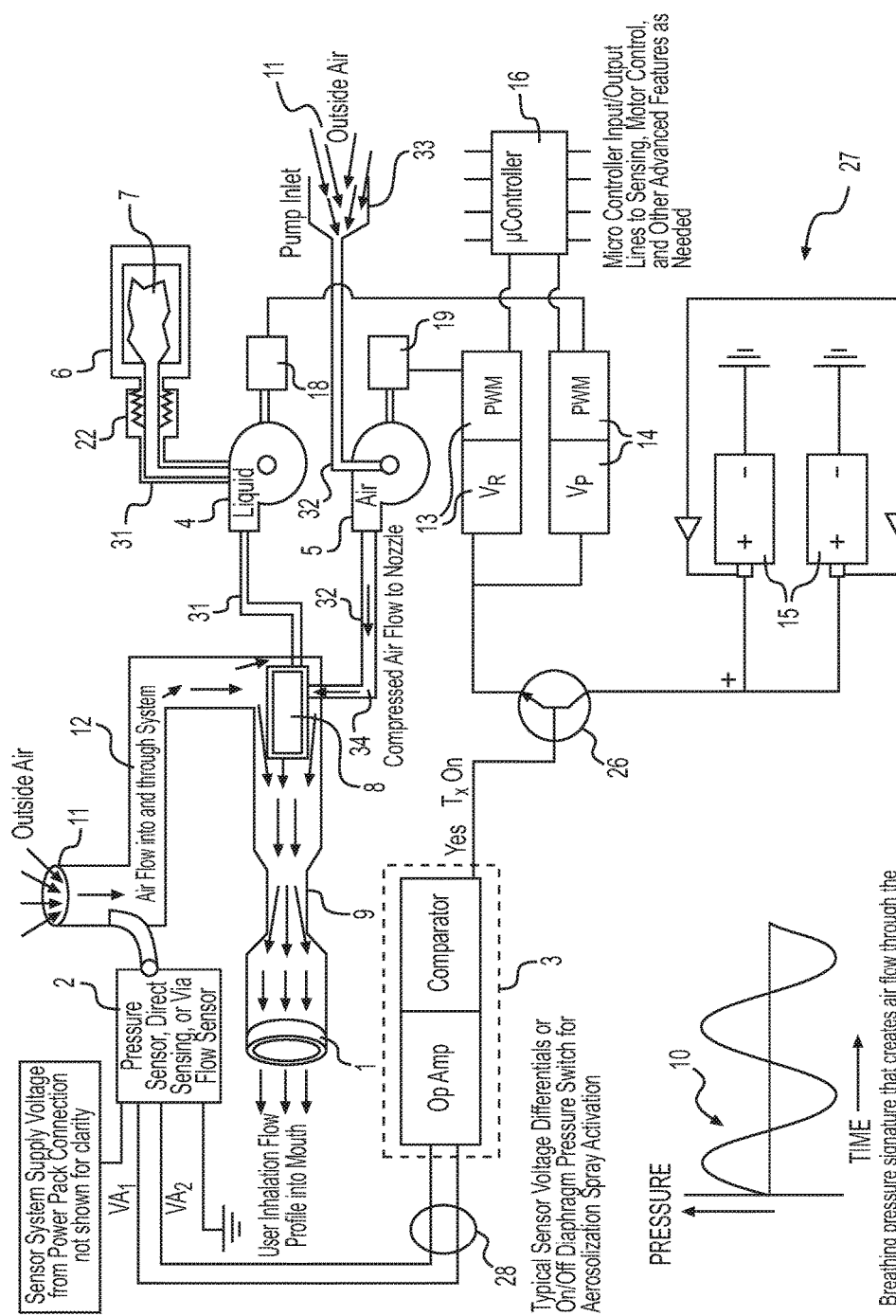
FIG. 1 is a functional diagram of the hand held device.
Figure 5:
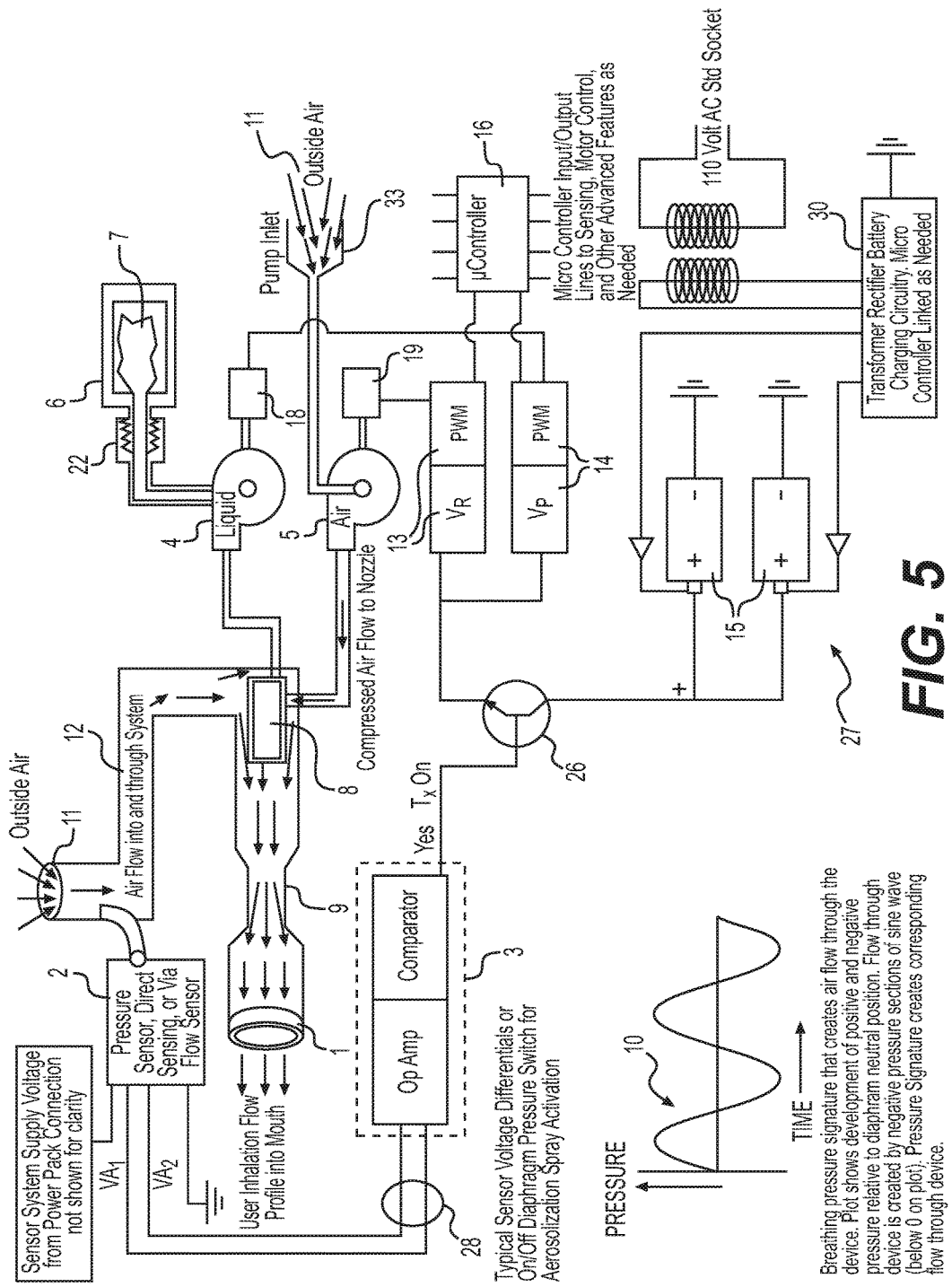
FIG. 5 replicates FIG. 1, but with the addition of charging circuitry.

FIG. 5 replicates FIG. 1 but with the addition of charging circuitry 30 to recharge the batteries 15.

While the invention has been described with reference to specific embodiments, modifications and variations of the invention may be constructed without departing from the scope of the invention.

The invention claimed is:

1. Apparatus comprising:
   a portable, hand-held aerosol inhaler having:
   a product reservoir containing a product to be delivered to a user,
   a product conduit connected to the reservoir,
   an air conduit,
   an air passageway through which outside air can flow through the apparatus,
   a mixing nozzle connected to the product reservoir via the product conduit and the air conduit for producing a first aerosolized mixture having a product and air mixture within the mixing nozzle and supplying the product and air mixture to the air passageway, wherein the product conduit and the air conduit are spaced from each other, wherein the product conduit and the air conduit each has a respective separate pathway directly connected to the mixing nozzle, and wherein the air passageway surrounds the mixing nozzle,
   a mouthpiece connected to the mixing nozzle via a throat for receiving the first aerosolized mixture with the product and air mixture and configured for aerosolized entrainment of the first aerosolized mixture with the product and air mixture in the outside air and forming a second aerosolized mixture and to pass the second aerosolized mixture into a mouth of a user during use,
   a pressure sensor connected to the air passageway and configured to detect inhaled breaths of the user, and to activate a selective dispensing of the second aerosolized mixture when the user inhales, and stopping delivery of the second aerosolized mixture when the user is not inhaling with sufficient negative pressure for entrainment,
   a product pump, wherein the product pump is configured to withdraw product from the reservoir by suction action of the product pump through the product conduit, and
   an air pump, wherein the air pump is connected to an inlet for supplying compressed air to the mixing nozzle through the air conduit.

2. The apparatus of claim 1, further comprising a collapsible bag in the reservoir containing the product, wherein the product pump is configured to withdraw product from the collapsible bag in the reservoir by the suction action of the product pump through the product conduit.

3. The apparatus of claim 2, wherein the product is a liquid and the reservoir is a liquid reservoir.

4. The apparatus of claim 3, wherein the liquid is configured to be pumped into the mixing nozzle from the product pump and air is configured to be compressed and pumped into the mixing nozzle by the air pump so that the liquid and air are combined to form the first aerosolized mixture and then expelled through an orifice of the mixing nozzle for creating the second aerosolized mixture for inhalation.

5. The apparatus of claim 1, wherein the pressure sensor is configured to send an electronic signal during inhalation by the user to activate the product pump and the air pump.

6. The apparatus of claim 1, further comprising a microcontroller which is configured to control amounts of air and liquid that are to be pumped into the mixing nozzle.

7. The apparatus of claim 1, further comprising two or more reservoirs containing different products connected to two or more product pumps respectively, wherein the two or more product pumps are configured to withdraw the different products from the two or more respective reservoirs.

8. The apparatus of claim 7, wherein the different products are two or more liquids and wherein a combination of the two or more liquids is configured to be created in the mixing nozzle when supplied by the two or more product pumps.

9. The apparatus of claim 1, further comprising rechargeable batteries to power the apparatus.

10. The apparatus of claim 1, wherein the aerosolized mixtures are an aerosolized medication.

11. The apparatus of claim 1, wherein the pressure sensor is an on/off diaphragm pressure switch.

12. The apparatus of claim 1, wherein the first and second aerosolized mixtures are configured to be dispensed only when negative pressure is measured by the pressure sensor.

13. A method comprising:
   providing an aerosol inhaler, the aerosol inhaler comprising:
   a product reservoir containing a product to be delivered to a user,
   a product conduit connected to the reservoir,
   an air conduit,
   an air passageway through which outside air can flow through the aerosol inhaler,
   a mixing nozzle connected to the product conduit and the air conduit for producing a first aerosolized mixture having a product and air mixture, wherein the product conduit and the air conduit are spaced from each other, and wherein the product conduit and the air passageway each has a respective separate pathway directly connected to the mixing nozzle, and wherein the air passageway surrounds the mixing nozzle,
   a mouthpiece connected to the mixing nozzle and to the air passageway via a throat,
   a pressure sensor connected to the air passageway to detect inhaled breaths of the user,
   a product pump, wherein the product pump is configured to withdraw product from the reservoir by suction action of the product pump through the product conduit, and
   an air pump, wherein the air pump is connected to an inlet for supplying compressed air to the mixing nozzle through the air conduit, forming a second aerosolized mixture by entraining the first aerosolized product and air mixture in the outside air from the air passageway, flowing the second aerosolized mixture through the throat and the mouthpiece into a user's mouth, when the user inhales through the mouthpiece, selectively dispensing the second aerosolized mixture when the user inhales producing sufficient flow to maintain entrainment, and stopping the delivery of the second aerosolized mixture when the user is not inhaling adequately for sufficient flow for entrainment.

14. The method of claim 13, further comprising activating the air pump and the product pump by the pressure sensor, and detecting the inhaled breaths.

15. The method of claim 14, wherein the product is a liquid and the reservoir is a liquid reservoir, and the product pump is a liquid pump.

16. The method of claim 15, wherein liquid pumped into the mixing nozzle from the liquid pump and air pumped into the mixing nozzle by the air pump are combined to make the first aerosolized mixture.

17. The method of claim 16, wherein the aerosol inhaler further comprises a microcontroller which controls the amounts of air and liquid that are pumped into the mixing nozzle.

18. The method of claim 15, wherein upon activation, the pressure sensor sends an electronic signal to power the liquid pump and the air pump.

19. The method of claim 13, wherein the aerosol inhaler further comprises two or more reservoirs containing different products connected to two or more product pumps, wherein the two or more product pumps withdraw the different products from the two or more respective reservoirs.

20. The method of claim 19, wherein the different products are two or more liquids and wherein a combination of the two or more liquids is created in the mixing nozzle.

21. The method of claim 13, further comprising providing rechargeable batteries to power the pumps.

22. The method of claim 13, wherein the aerosolized mixtures are an aerosolized medication.

23. The method of claim 13, wherein the pressure sensor comprises an on/off diaphragm pressure switch.

24. The method of claim 13, comprising dispensing the second aerosolized mixture only when sufficient negative pressure is measured by the pressure sensor.

* * * * *